United States Patent [19]

Ballard et al.

[11] Patent Number: 4,482,438

[45] Date of Patent: Nov. 13, 1984

[54] METHOD OF PERFORMING A CHEMICAL REACTION

[75] Inventors: Roy E. Ballard, Norwich; Alexander McKillop, Honingham, both of England

[73] Assignee: National Research Development Corporation, London, England

[21] Appl. No.: 520,646

[22] Filed: Aug. 5, 1983

[30] Foreign Application Priority Data

Aug. 11, 1982 [GB] United Kingdom ............... 8223071

[51] Int. Cl.³ .............................................. C25B 3/02
[52] U.S. Cl. ....................................... 204/78; 204/72; 204/59 R
[58] Field of Search ................... 204/59 R, 78, 79, 80, 204/72

[56] References Cited

U.S. PATENT DOCUMENTS 3,953,305  4/1976  Connolly ............................... 204/97
4,329,208  5/1982  Vayenas ................................ 204/80

FOREIGN PATENT DOCUMENTS 313352   6/1929  United Kingdom .
1203434  8/1970  United Kingdom .

OTHER PUBLICATIONS

Clark et al., "Chemistry in Britian" Feb. 1975 (pp. 59–64).

Primary Examiner—John F. Niebling
Attorney, Agent, or Firm—Cushman, Darby & Cushman

[57] ABSTRACT

A streamline flow of aqueous cobalt (II) sulphate solution passes through a platinum tube which, as an anode, electrolyses the solution to cobalt (III). The flow, with a high surface concentration of nascent cobalt (III), falls into a volume of 1-methylnaphthalene in an organic solvent, and is recovered from underneath for recycling to the platinum tube anode.

The cobalt (III) reacts with the 1-methylnaphthalene to form 1-naphthaldehyde. Other oxidations of organic reactants using nascent high-oxidation-state aqueous metal ions are also disclosed.

20 Claims, 12 Drawing Figures

METHOD OF PERFORMING A CHEMICAL REACTION

The invention relates to a method of performing a chemical reaction between a reactive species and a reactant and is suitable for cases where the reactive species cannot be formed in the presence of the reactant, particularly where the reactive species has a limited lifetime (such as because of spontaneous decay or a propensity to engage in unwanted reactions).

According to the invention, a method of performing a chemical reaction between a reactive species and a reactant comprises flowing a liquid including the precursor of the reactive species past an electrode for forming the reactive species from its precursor, causing the liquid to flow out of the influence of the electrode (and of anything else that would react with the reactive species), and preferably immediately after passing the means, and certainly within 100 milliseconds, contacting the liquid with a volume of liquid comprising the reactant, the two liquids being substantially immiscible, whereby the reactive species reacts preferentially with the reactant.

The flow leaving the electrode, and when it passes into the volume, or both, may be streamline. In that case, the reactive species (having been formed either at the surface or within the flow) tends to be preserved, even if it is reactive towards the rest of the liquid, because its station in the flow does not change. In the case of streamline flow, a high superficial concentration of reactive species can be preserved downstream, which may assist the desired chemical reaction because the reactant 'sees' firstly the flow surface. However, in other cases it may be tolerable or even advantageous for the flow to be turbulent on leaving the electrode and/or contacting the volume.

The electrode activates the precursor to form the reactive species. The counterelectrode may be disposed upstream of the electrode (optionally in the core of the flow if that is to be streamline or separated from the electrode by a membrane), so that the liquid which has contacted it makes no, or negligible, contact with the reactant, and it is certainly preferably disposed such that no electrolysis of the reactant occurs. The electrode or the counterelectrode can be earthed. The electrode may be a conducting orifice. The electrode may comprise a plurality of orifices arranged in parallel and electrically interconnected, such as a metal watering-can rose.

The volume of the reactant, if the reactant is less dense than and insoluble in the said precursor, may float as a layer on a volume of the precursor, which may be recirculated to the said surface.

The electrode may be anodic. The reactive species may be in aqueous solution, such as lead ion, cerium ion, manganese ion, silver ion or cobalt ion. The reactant may be organic and may be non-conductive, such as 1-alkylnaphthalene (which may be substituted), 1-alkoxynaphthalene, 1-naphthylalkanol, toluene (which may be substituted), cymene or methylanthracene.

The electrochemical method according to the invention offers various advantages over wet chemical and standard electrochemical methods. The reactive species may be continuously regenerated in a recirculating system, thus alleviating the need of using stoichiometric or excess amounts of precursor. This reduces chemical costs and the problems associated with disposing of large amounts of chemical waste. Also, since the reactive species is produced in situ, the need of maintaining a stock of unstable chemicals is eliminated. The method furthermore enables the exploitation of species which are so unstable that they cannot be stored at all. The instability may be due to disproportionation, spontaneous decay, solvation, etc. Even nominally stable reactive species such as Co(III) are more reactive in the first tens of milliseconds after they are formed. The method according to the invention brings the reactive species into contact with the reagent while they are still in this 'more reactive' condition. Not only are fresh, nascent or metastable species more reactive, but also the apparent surface tension of the flow changes in the first tens of milliseconds, slowing reaction across the interface between the two liquids. Thus the liquid containing the reactive species preferably contacts the volume of the liquid containing the reagent within 50 milliseconds (e.g. about 30 milliseconds), more preferably within 20, or 10, milliseconds of leaving the electrode.

In the electrochemical method, since the organic reactant reacts with the reactive species, there is no need for it ever to make contact with an electrode. The problems of electrode polarisation and electrode surface reactions due to the presence of the reactant at the electrode are therefore avoided.

The invention will now be described by way of example with reference to the accompanying drawings, in which.

Figure 1:
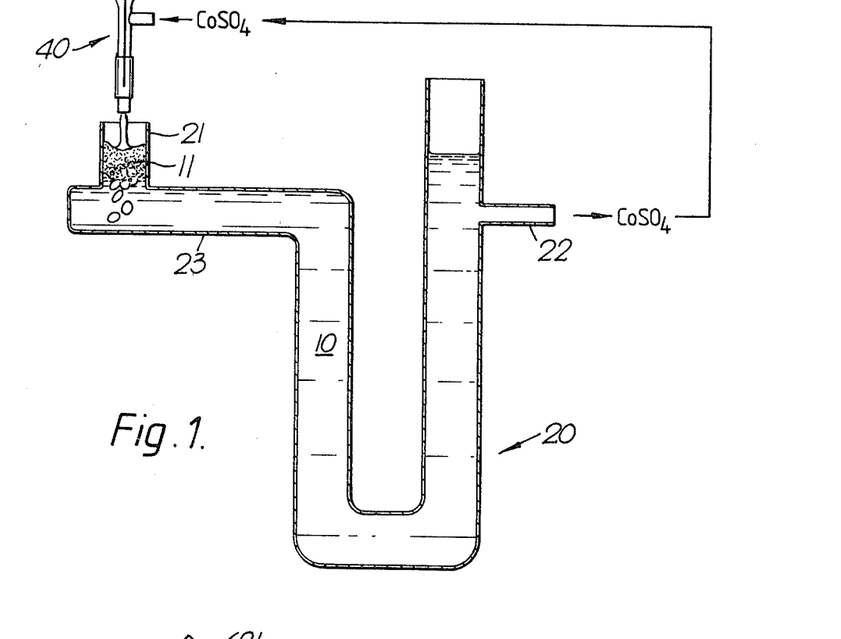
FIG. 1 is a schematic illustration of a cell in which the method according to the invention may be performed.

In FIG. 1, a generally sickle-shaped glass tube 20 of volume 550 ml has an upstanding open-topped upright entrance pipe 21 leading to the 'handle' of the sickle, and an exit pipe 22 at the far end of the sickle whose 'blade' end is open. An electrode assembly 40, to be described more fully under FIG. 4, contains an anode and a cathode, and receives (via a pump and flow regulator, now shown) liquid from the exit pipe 22, electrolyses the surface of a streamline flow thereof, and allows the flow (still streamline) to fall into the entrance pipe 21.

In use, the tube 20 contains a liquid 10, for example 550 ml of aqueous solution of 0.12M cobalt sulphate, to a level somewhat above the base of the entrance pipe 21. (The exit pipe 22 is set slightly lower.) In the entrance pipe 21, on the liquid 10, there floats an organic layer including a reactant 11, of a total volume of 5 ml and occupying a height in the pipe 21 of 11 mm. The organic layer is immiscible with the aqueous liquid 10, and is for example 1-methylnaphthalene (reactant 11) dissolved in tributylphosphate. The electrode assembly 40 is 10 mm clear of the reactant 11.

In typical use the streamline flow issuing from the assembly 40 takes about 30 milliseconds to reach the reactant 11.

When the streamline flow enters the reactant 11, the surface of the flow makes contact with the reactant and it is precisely at the surface that there is a high concentration of the reactive species (Co(III) in this case) which will react efficiently with the reactant (in this case, 1-methylnaphthalene).

The liquid 10 passes through (and, as appropriate, reacts with) the reactant 11, re-emerging into the body of liquid 10 contained in tube 20. There is a drift in the tube 20 from the entrance pipe 21 to the exit pipe 22 because of the action of the pump which is supplying the electrode assembly 40 with the liquid 10.

The electrode assembly 40, being self-contained, applies an electric field across the aqueous liquid 10 only; the reactant 11 is no subject to electrolysis. The tube 20 has a crank or offset 23 (the 'handle' of the sickle) with a right angle at each end. This baffles the flow which has traversed the layer of the reactant 11 and has the effect of reducing the amount of the reactant 11 carried along with the drift of the circulating liquid 10, and makes it possible to run the cell continuously for long periods, e.g. overnight.

Figure 2:
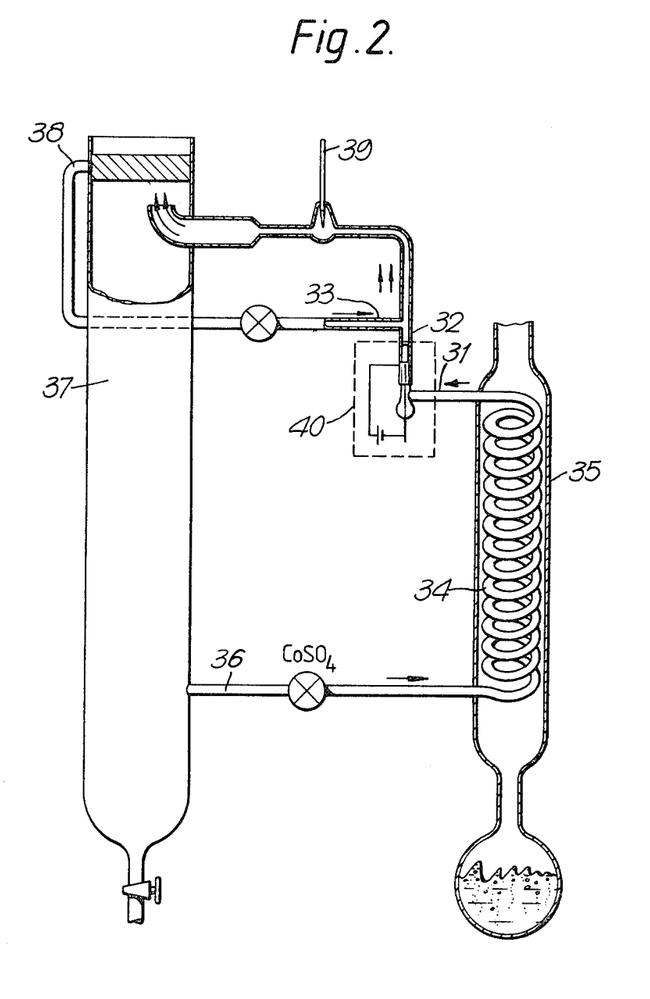
FIG. 2 is a schematic illustration of a modified cell in which the method according to the invention may be performed.

Turning now to FIG. 2, a cell for performing the method according to the invention comprises an electrode assembly 40 (to be described more fully under FIG. 4) containing an anode and a cathode, receiving an aqueous liquid at 31 and electrolysing the surface of a streamline flow thereof which is discharged through a smooth-walled pipe 32 connected without a break to the assembly 40.

A pumped organic reactant (less dense than the aqueous liquid) joins the pipe 32 through a T-junction inlet 33. The resulting mixture passes a thermometer 39 on its way to a settling/filtration column 37. The organic phase (resulting from the contact of the freshly electrolysed aqueous liquid with the organic reactant) will settle towards the top of the column 37 where it is removed via an off-take 38 from which product may be extracted or, as appropriate, it is recycled via an independent pump to the inlet 33 for more reaction. The aqueous liquid settles to the bottom of column 37 through a filter bed and is removed from a bottom-offtake 36 for recycling to the electrode assembly 40 at 31 via a heated coil 34 whose temperature is controlled by surrounding the coil with the vapours of a refluxing liquid in a condenser 35.

In this design, both the aqueous electrolyte and the organic phase are being independently pumped. The two phases are forced together at a T-junction that is in line directly after the platinum tube anode. After the two phases are forced together, the flow stream passes a thermometer 39 and then enters the column 37 which separates the less dense organic phase from the electrolyte. The organic phase is pumped through a flow controller and is sent back to the T-junction. The electrolyte is passed through a glass bead/glass wool filter bed, then is pumped through its flow controller and on to the electrode assembly 40. The purposes of this design of apparatus are (1) to mix the two phases immediately after the electrolyte has passed through the anode, (2) to mix the two phases thoroughly, (3) to lengthen the contact time between the two phases.

Figure 3:
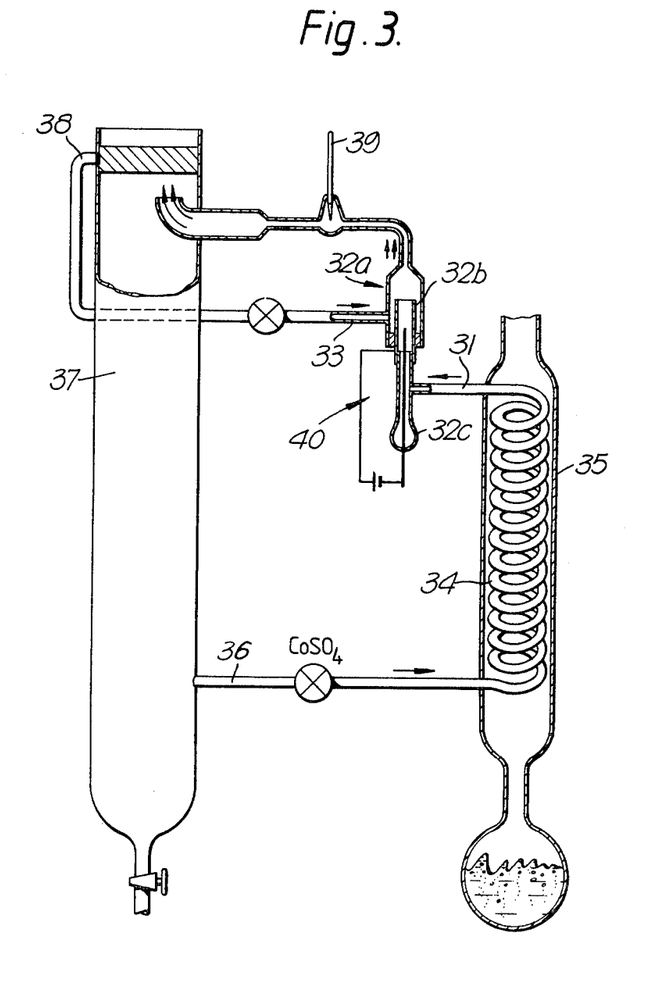
FIG. 3 is a schematic illustration of a further modified cell in which the method according to the invention may be performed.

Turning to FIG. 3, a cell for performing the method according to the invention is identical to the cell of FIG. 2 except for the arrangement of the electrode assembly 40. In this assembly 40, aqueous liquid enters at 31 and passes, round a right angle, into a tubular cylindrical platinum anode 32b. The right angle has another branch colinear with 32b leading into a glass dead-end 32c which could be separated from the main stream of aqueous liquid by a semipermeable membrane or frit for purposes discussed below; in this actual example we had no such separation.

The organic phase from inlet 33 is forced together with the aqueous phase, not at a T-junction as was the case in FIG. 2, but in a concentric flow arrangement 32a (where being no pipe 32 in this Figure). The organic phase is pumped to a chamber surrounding the tubular cylindrical anode 32b through which is pumped, in streamline flow, the aqueous phase. At the instant of leaving the anode, the aqueous phase meets the organic phase which is being pumped co-current with it.

The description for FIG. 2 applies to the cell of FIG. 3 in all other respects. Thus, the phases forced together in the arrangement 32a then pass a thermometer 39, and so on as in FIG. 2.

Figures 4, 5:
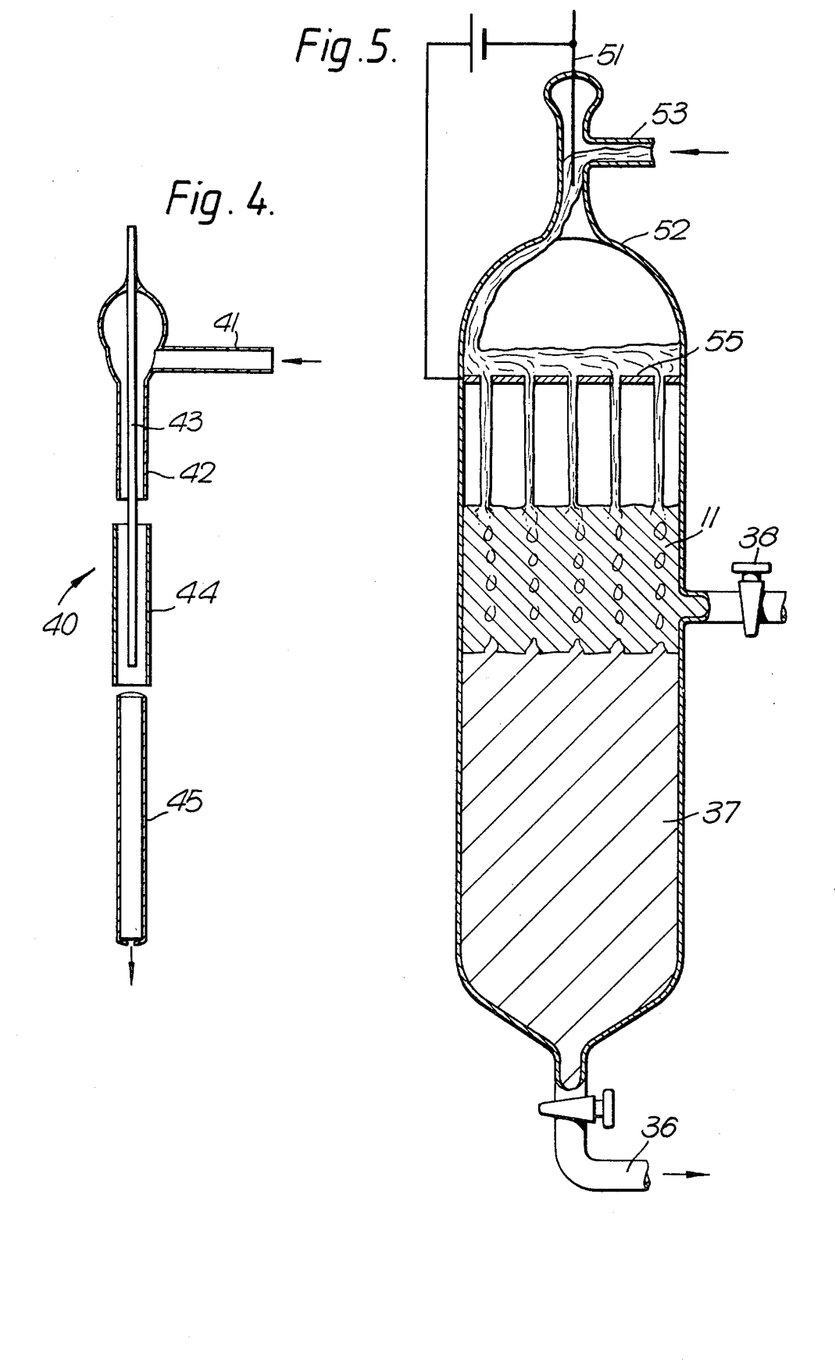
FIG. 4 is an exploded view of an electrode assembly which is used in the cells of FIGS. 1 and 2.
FIG. 5 is a schematic illustration of a cell in which the method according to the invention may be performed using a different electrode arrangement from that of FIG. 4.

Turning now to FIG. 4, the electrode assembly 40 used in the cells of FIGS. 1 and 2 is shown in exploded view. The liquid to be electrolysed enters, via a feed pipe 41, into a smooth walled cylindrical duct 42 containing an axial tungsten counterelectrode 43. An inert plastics connecting collar 44 fits over the duct 42 and into the collar 44 is slid, to abut the duct 42, a platinum tube 45 as the electrode. Liquid emerges from the electrode 45, if desired in streamline flow, with its surface having a high concentration of electrolysed species. The electrode tube 45 extends downstream of the counterelectrode 43, so that electrolysis is confined to the aqueous liquid, i.e. is negligible downstream of the tube 45.

In a possible modification, the counterelectrode 43 is withdrawn into the bulbous part above the feed pipe 41. A sintered glass membrane (not shown) divides the bulbous part from the rest of the electrode assembly. In this way, counterions produced at the counterelectrode 43 do not enter the aqueous liquid stream. Also, platingout of the circulating metal ion can thereby be prevented.

Figure 6:
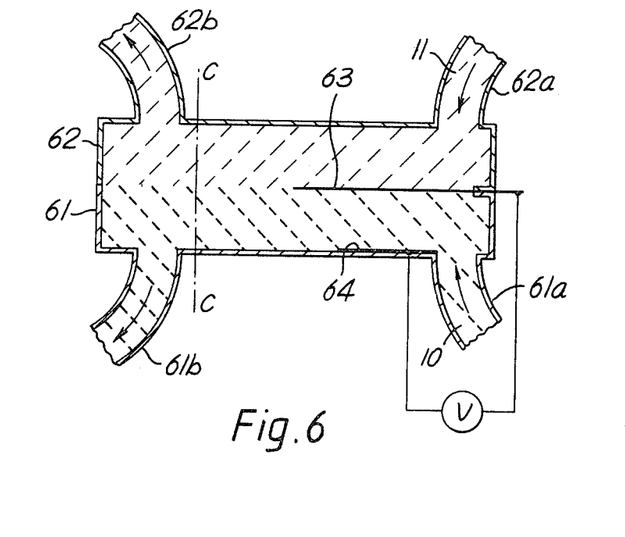
FIG. 6 is a schematic illustration of a different cell in which the method according to the invention may be performed.
Figure 7:
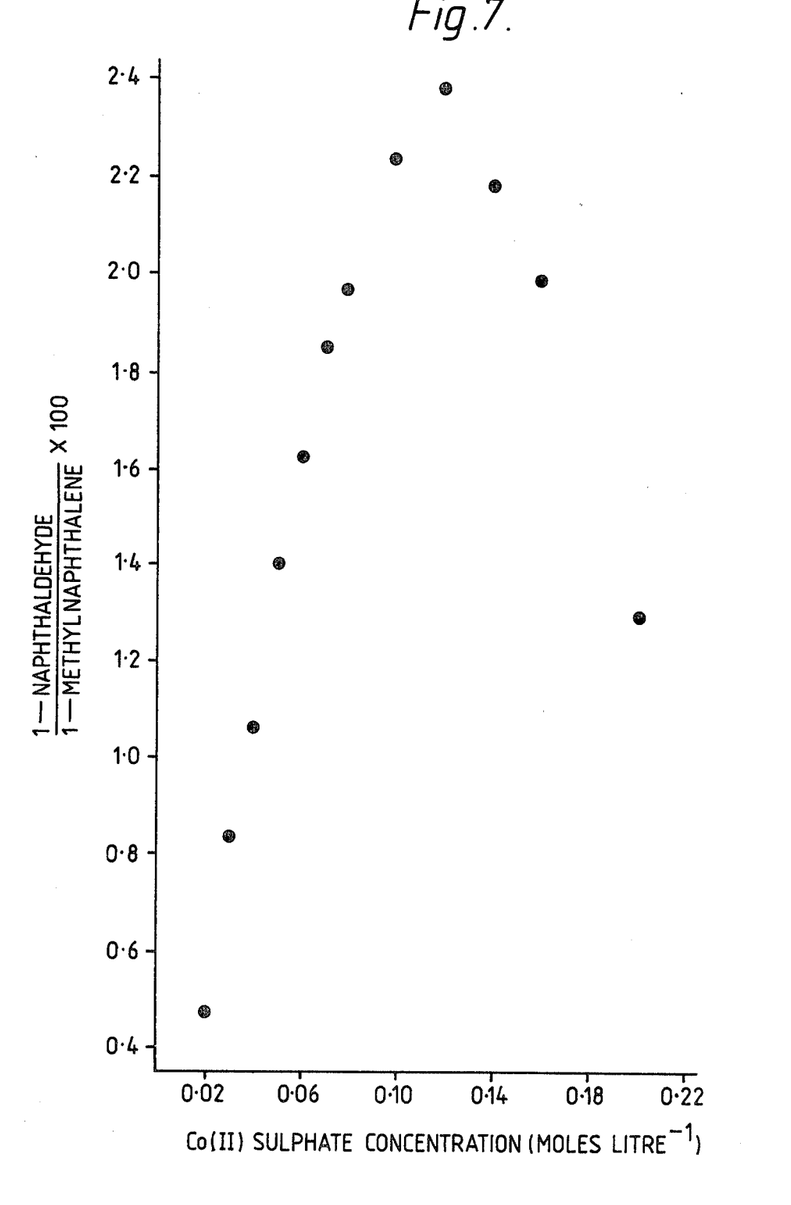
FIGS. 7 to 12 illustrate the effect of varying selected parameters on the progress of a reaction performed by a method according to the invention.

In FIG. 6, a cell for performing the method according to the invention comprises two open-topped hollow rectangular blocks 61 and 62 mounted face-to-face ('open top to open top'). The blocks 61 and 62 are mirror-images of each other, and the block 61 has an inlet 61a opposite the open face and an outlet 61b also opposite the open face but at the other end of the block 61. Likewise, the block 62 has an inlet 62a and an outlet 62b. An electrode 63, of thin platinum foil, is clamped between the blocks between the two inlets and extending some little way downstream. A counterelectrode 64 is cemented adjacent to the inlet 61a, and a desired voltage can be applied between the electrode by a potential source V.

In use, an aqueous solution 10 (e.g. of cobalt sulphate) is pumped through the inlet 61a and flows as a sheet across the block 61 and out through the outlet 61b. At the electrode 63, Co(III) ion is continuously generated, and tends to stay concentrated at the upper surface of the sheet flow as it moves towards the outlet 61b. Meanwhile, a (less dense) organic phase 11, such as 1-methylnaphthalene dissolved in tributylphosphate, is pumped through the inlet 62a and flows as a blanket floating on top of the aqueous solution 10, across the block 62 and out through the outlet 62b. The flow directions of the phases 10 and 11 are the same, but the speeds of the two flows may be the same or different, as required, being variable by adjusting the respective volumetric pumping rates. Reaction takes place across the (horizontal) interface between the phases.

In a modification, the cell is truncated on the line c—c, and placed on end, with the inlets 61a and 62a uppermost. The blocks 61 and 62 are simply cut open, with the outlets 61b and 62b absent. The phases 10 and 11 then share a vertical interface across which reaction proceeds. The phases may empty into a settling tank, in which they separate. Phase separation can be achieved with a less precise control than may be desirable with the cell of FIG. 6.

In use, the cell shown in FIG. 1 is charged with the desired electrolyte solution (550 ml of 0.12M cobalt sulphate in sulphuric acid). A flow is established and adjusted by means of the pump and flow controller. The temperature of the electrolyte is adjusted to the desired level by immersing the U-tube 20 into an appropriately heated oil bath and is measured at the point where the flow stream enters the bulk of the solution. With certain apparatus, it is found that the flow rate varies with temperature and in such cases the flow rate must be constantly adjusted until the system reaches thermal equilibrium.

The desired current is established and a 2 to 4 ml quantity of the organic reactant 11, optionally in organic solution, for example 2 ml 1-methylnaphthalene in 3 ml of tributylphosphate, is floated as a layer in the entrance pipe 21. At this point the flow rate and the position of the tube electrode may have to be readjusted and the bottom of the electrode assembly 40 is set to be 10 mm above the top of the organic layer. The optimum flow rate varies from reaction to reaction. When the flow rate is too fast, the organic phase tends to be swept away by the flowing electrolyte.

The flow rate needed to achieve the proper level of mixing action depends on a number of factors. One is the density of the electrolyte. If the density of the two phases is very similar, then the organic phase is swept away even at very low flow rates. The second factor which determines the rate of flow is the amount of organic phase used. Larger volumes of organic phase allow higher flow rates. A third factor is the composition of the organic phase. Physical properties such as density, surface tension and viscosity influence the reaction under a given set of conditions. Tributylphosphate is a solvent that gives the organic phase the physical properties required for good yield at a reasonable flow rate. A fourth factor is the gap between the tip of the jet electrode and the surface of the organic phase; see FIG. 10.

After the reaction is stopped, the reaction mixture (organic phase and electrolyte) is 'isolated' from the apparatus by pumping the reaction mixture into a 1 liter conical flask. Any liquid that remains in the apparatus after pumping, for example the liquid in the U-tube, is poured into this flask as the apparatus is disassembled. Each piece of the apparatus, including the tubing, jet electrode and pump, is rinsed with an organic solvent (for example diethyl ether) and the rinses are combined with the rest of the reaction mixture. Finally, all the pieces of the apparatus are washed with water and acetone, then dried with an air stream.

The organic and aqueous phases from the 'isolated' reaction are separated and, in our preferred procedure, the aqueous phase is extracted three times with an organic solvent (usually diethyl ether). The combined organic portions are washed with water and then extracted with a saturated $NaHCO_3$ solution. The organic portion is washed with water, a saturated NaCl solution and then dried over $MgSO_4$. Filtration and solvent removal yield the crude organic mixture.

The $NaHCO_3$ extract is washed with an organic solvent and then made acidic with a 10% HCl solution. The resulting solution is extracted three times with an organic solvent and the combined extract is warmed with water. Drying over $MgSO_4$, filtration and solvent removal yield any acidic materials.

Turning to FIG. 5, a cell is shown which, although related to that in FIG. 1, offers the prospect of faster throughput.

A tungsten cathode 51 projects into a dome 52 (of glass or other smooth-surfaced non-conductive material). An inlet 53 for a pumped aqueous phase is arranged to pour a continuous stream of liquid over the cathode 51 and down the inside of the dome 52. A apertured platinum foil anode 55 forms a floor to the dome 52, and a certain depth of liquid covers this floor. The starting and steady-state rates of pumping the liquid must be so controlled as to achieve this.

The anode 55 acts as a shower head or watering-can rose. Examples of its size are:

|  | (a) | (b) | (c) |
| --- | --- | --- | --- |
| Diameter of anode: | 2 cm | 1 cm | 1 cm |
| No. of apertures: | 7 | 4 | 1 |
| Diameter of each aperture: | 0.8 mm | 0.8 mm | 0.8 mm |

Streams of liquid from the anode 55 fall through space for a distance of 15 mm before landing on an organic layer containing an organic reactant 11. This layer, being less dense than the aqueous phase, floats on top of it and the streams falling from the anode 55 pass downwards through, and react with, this layer, then join bulk aqueous phase in a settling column 37. In the Figure, the streams are shown as traversing the layer in drops but this is purely for illustration.

A take-off 38 is provided so that the organic layer can be removed in batches for recovery of the product as required. At the base of the column 37, lower than any substantial quantity of the organic layer is ever swept or entrained, a take-off 36 returns the aqueous phase to a pump and temperature controller for recycling to the inlet 53.

The use of the cells described will now be explained by way of example with reference to specific reactions.

REACTION 1

Oxidation of 1-methylnaphthalene

Using the electrode assembly of FIG. 4 and the cell of FIG. 2, cobalt(III) sulphate was prepared by anodic oxidation of Co(II) sulphate in a 2M $H_2SO_4$ solution:

The anode was of platinum, which has lasted over 1000 hours. Graphite could have been used, but suffers the disadvantage of decomposition over time when a current is passed through it. Other anode materials, such as lead, tungsten and molybdenum, were unsuccessful.

When the electrochemically generated Co(III) sulphate laminar jet stream is allowed to react with 1-methylnaphthalene in the pipe 21, the only isolated product is 1-naphthaldehyde.

The optimum reaction temperature is between 37° and 40° C. and the 1-methylnaphthalene may be used neat or with a solvent. An appropriate solvent are tributylphosphate. Th data from a typical run is as follows:

| Starting Material | 14 mmol 1-methylnaphthalene |
|---|---|
| Solvent | tributylphosphate, same volume as the Starting Material |
| Electrolyte composition | 0.12 M Co (II) sulphate in 2 M $H_2SO_4$ |
| Anode material | platinum |
| Current | 200 mA |
| Current density | 350 $Am^{-2}$ |
| Reaction temperature | 37–40° C. |
| Reaction time | 21 hours |
| Conversion of starting material | 5.9 mmol 42% |
| Yield of isolated aldehyde | 2.2 mmol 37% |
| Electrochemical yield | 5.6% |

The same reaction was tried in a modified cell, without the crank 23. 2 g (14 mmol) of 1-methylnaphthalene in 3 g of tributylphosphate was allowed to react for 40 hours with electrochemically produced Co(III) sulphate at 40°–45° C. The electrolyte solution was composed of 0.12M Co(II) sulphate in 2M $H_2SO_4$. The current was 200 mA. The organic material isolated from this run was placed on a silica gel column, which was eluted with a solution of 5% ether in petroleum ether (bp=60°–80° C.). The initial band consisted of 860 mg (6 mmol, 43%) of starting material. The second band yielded 447 mg (2.9 mmol) of 1-naphthaldehyde. The aldehyde yield was 36% based on consumed starting material. The aldehyde yield was 36% based on consumed starting material. The infrared spectrum of the product was identical to that of an authentic sample.

The same reaction was tried using a different aqueous electrolyte. 1 g (7 mmol) quantity of 1-methylnaphthalene in 3 ml of tributylphosphate was allowed to react with electrochemically produced Co(III) tetrafluoroborate at 23° C. The electrolyte solution was composed of 0.03M Co(II) tetrafluoroborate in 40% $HBF_4$. The reaction was run for 21 hours at 200 mA. The organic reactant and products were isolated using dichloromethane as the organic solvent. The organic material obtained was placed on a silica gel column, which was eluted with petroleum ether (bp=60°–80° C.). The initial band yielded 789 mg (79%) of starting material. The solvent was changed to 2% ether in petroleum ether and a second band eluted which yielded 51 mg of a colourless viscous oily multicomponent mixture that consisted mainly of 4,4′-dimethyl-binaphthyl; no further attemps at purification were made.

Reaction 1 was then more systematically investigated, using the cell of FIG. 1 and the electrode assembly of FIG. 4.

The following parameters were examined in turn: cobalt sulphate concentration (otherwise held at 0.05M when the other parameters were being varied); sulphuric acid concentration (otherwise held at 2½M when the other parameters were being varied); temperature (otherwise held at 40° C. when the other parameters were being varied); the weight percentage of 1-methylnaphthalene, of which 3 g always was used in the organic phase (the solvent making up the balance being tributylphosphate) (this value being otherwise held at 50% when the other parameters were being varied); and current density (platinum tube anode 6 cm long and of 3.5 mm internal diameter) (the current density being otherwise held at 303 $A/m^2$ when the other parameters were being varied). The results will be described in relation to FIGS. 7, 8, 9 and 10 respectively, there being no figure devoted to temperature. In all cases, the reaction was run for 2½ hours. Those parameters are shown on the abcissa of each figure, and the ordinate is in arbitrary units of (aldehyde/1-methylnaphthalene).

Cobalt(III) is a suitable reactive intermediate for use in these 'jet' electrochemical reactions. This species is readily prepared by the anodic oxidation of Co(II) in an acid solution.

Figure 8:
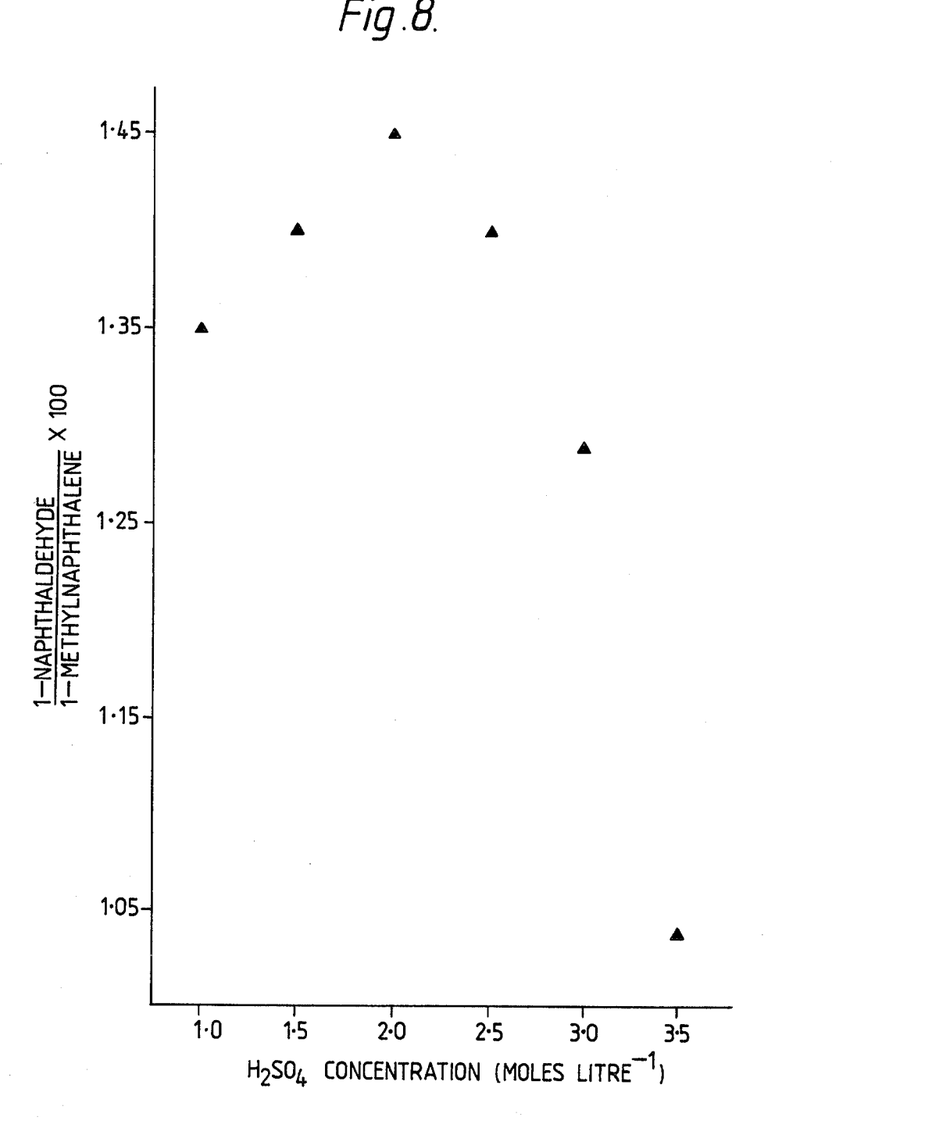

Cobalt(III) sulphate solutions are unstable, but have a sufficient lifetime to be utilized for reactions with organic reactants. The production of 1-naphthaldehyde as a function of cobalt concentration is shown in FIG. 6, from which an optimum [Co] of 0.12M (say 0.06 to 0.18M, preferably 0.08 to 0.16M, more preferably 0.10 to 0.14M) can be deduced. FIG. 8 shows reaction yields as a function of sulphuric acid concentration in the electrolyte. The concentration of $H_2SO_4$ should be 1M to 3M, preferably 1½M to 2½M.

The optimum temperature range for this reaction is between 40° and 45° C. Cobalt(III) becomes less reactive with 1-methylnaphthalene at lower temperatures, and in fact, at 20° C. visible concentrations of Co(III) sulphate become present in this apparatus as the electrolyte turns blue from its original pink colour. Higher reaction temperatures apparently cause the rate of reduction of Co(III) to increase to the extent that it does not have an opportunity to react with the organic reactant.

Figure 9:
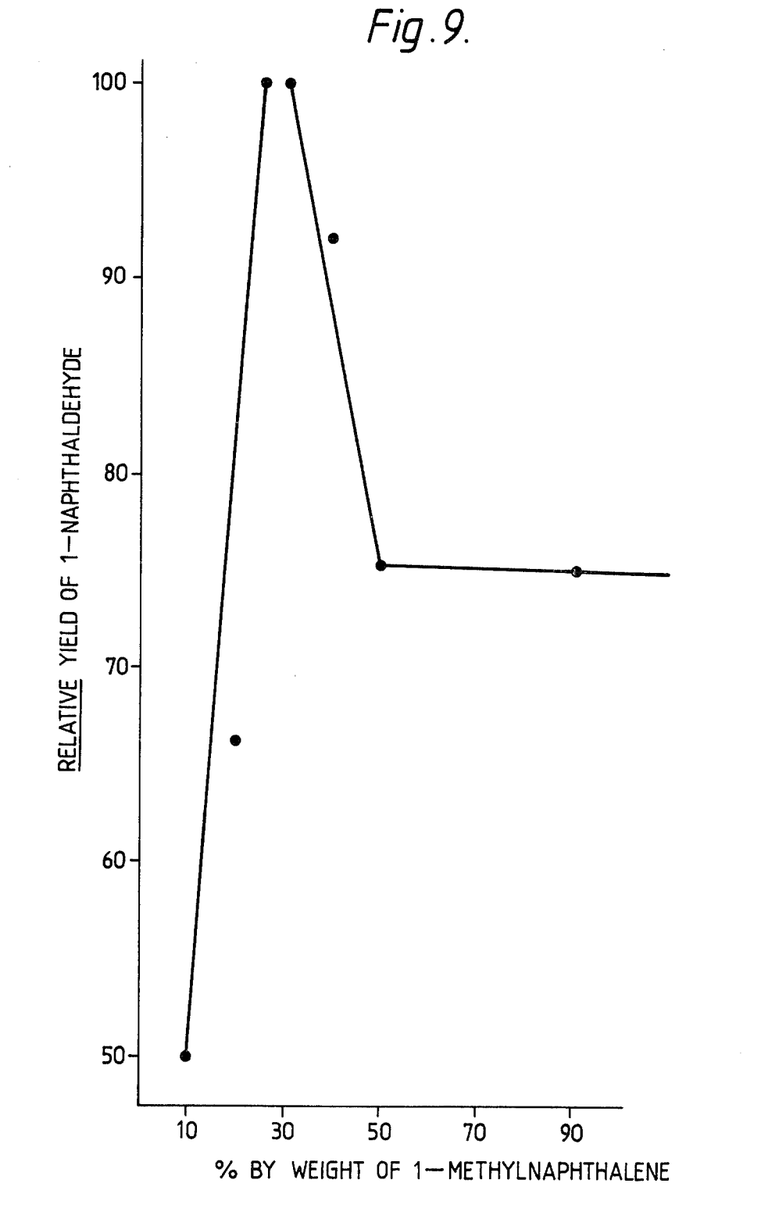

As shown in FIG. 9, the optimum concentration range of 1-methylnaphthalene in tributylphosphate is between 25 and 40% by weight. At concentration of 50% and above, the beneficial effect of the polar tributylphosphate is gone and aldehyde production remains constant.

Figure 10:
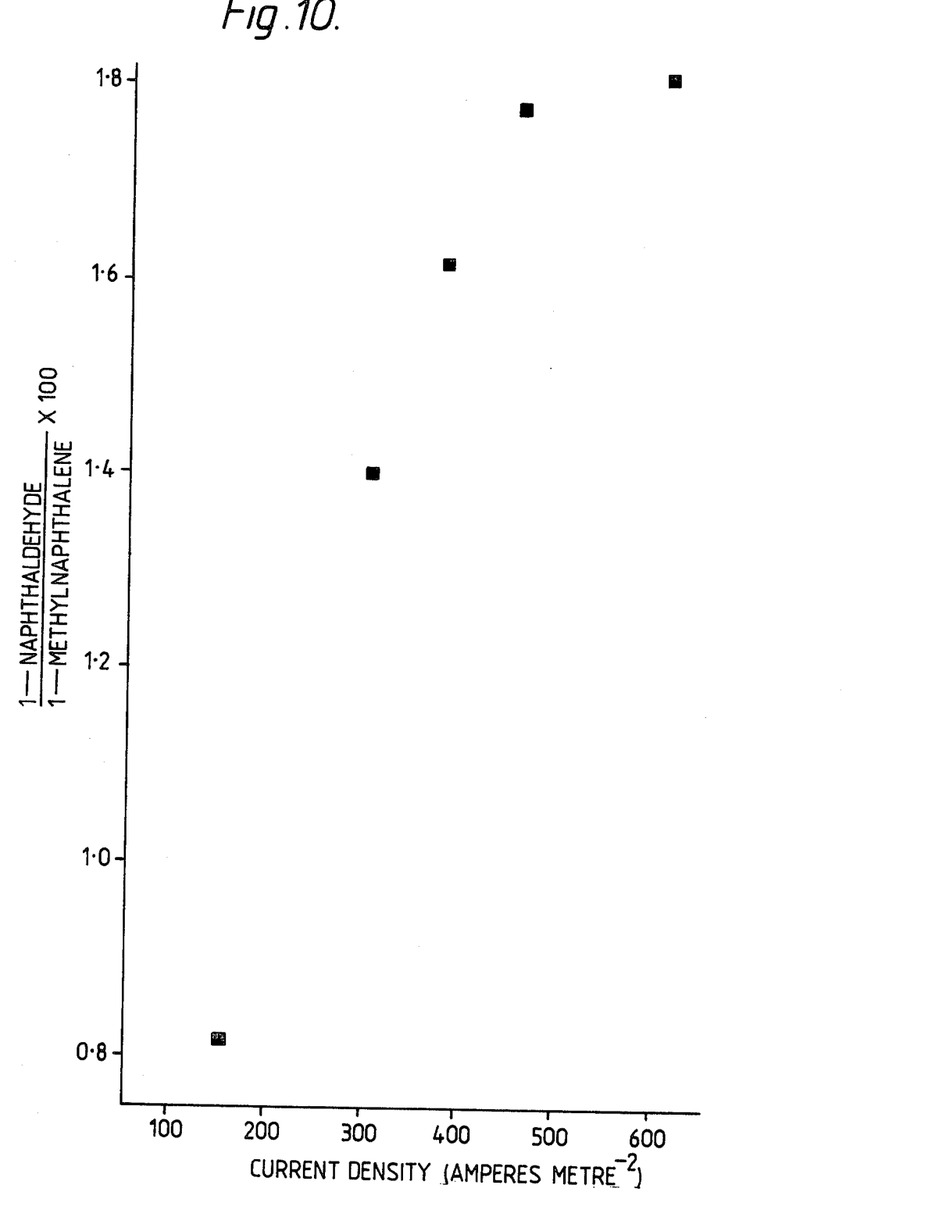

As shown in FIG. 10, increased current density increases the production of aldehyde until it reaches 454 $Am^{-2}$ (platinum tube anode, 6 cm length, 3.5 mm internal diameter). Above this current density, aldehyde production remains almost constant. The data also show that increased current density decreases the current efficiency. In other words, there is less aldehyde formed per coulomb used at higher current densities. Therefore, if to produce a certain amount of aldehyde a low current density is used, the reaction will have a greater current efficiency but a slower rate than if the reaction were carried out at a higher current density.

Using the cell of FIG. 1, therefore, it was found useful to circulate 550 ml of aqueous electrolyte—0.12M cobalt sulphate in 2M sulphuric acid—at the rate of 100 ml min$^{-1}$ into 2 ml 1-methylnaphthalene (4.5M in tributylphosphate solution) at 40°–45° C., for 20 hours at 2.8 V. 36% of the 1-methylnaphthalene was converted to aldehyde.

Using the cell of FIG. 3, the above values were copied except as follows. The recirculation of the aqueous electrolyte was at the rate of 70 ml min$^{-1}$. The organic reagent was also circulated, also at the rate of 70 ml min$^{-1}$. The cell voltage was 2.3 to 2.8. The duration of the run was 200 hours. 12% of the 1-methylnaphthalene was converted to aldehyde.

The above cell voltages represented currents of 200 mA and current densities on the anode of 303 Am$^{-2}$.

Cerium(IV) can be used in place of cobalt(III), sometimes with increased yield; a convenient solution is 0.084M cerium(III) sulphate in 2M sulphuric acid.

Figure 11:
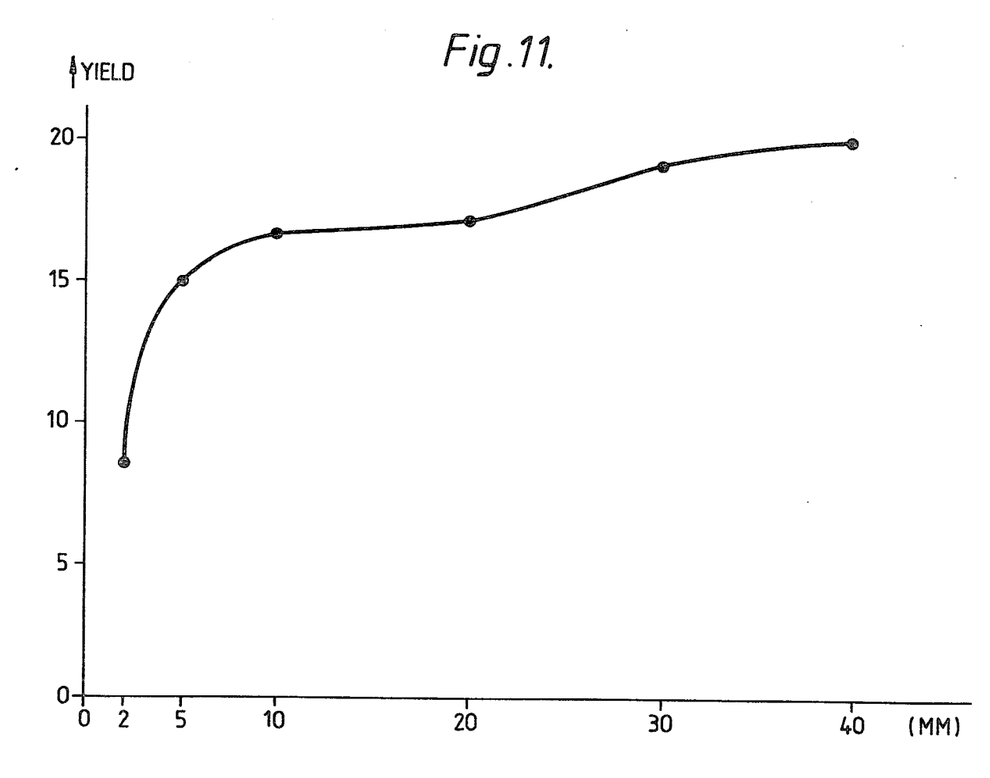

FIG. 11 shows how the yield of 1-naphthaldehyde varies (all other parameters being held constant) as the distance between the bottom tip of the tube electrode 45 and the top of the organic layer including the reactant 11 varies in the cell of FIG. 1. A distance of 10 mm is believed to correspond with a time of passage through space of about 30 ms. The abcissa is the distance in mm, and the ordinate is the yield in arbitrary units of (aldehyde/1-methylnaphthalene). It is clearly worth having a distance of at least 10 mm where possible, but increasing it above 10 mm, even up to 40 mm, brings only marginal extra benefit. (Even at 40 mm, the jet was so run as to stay as continuous streamline flow).

Figure 12:
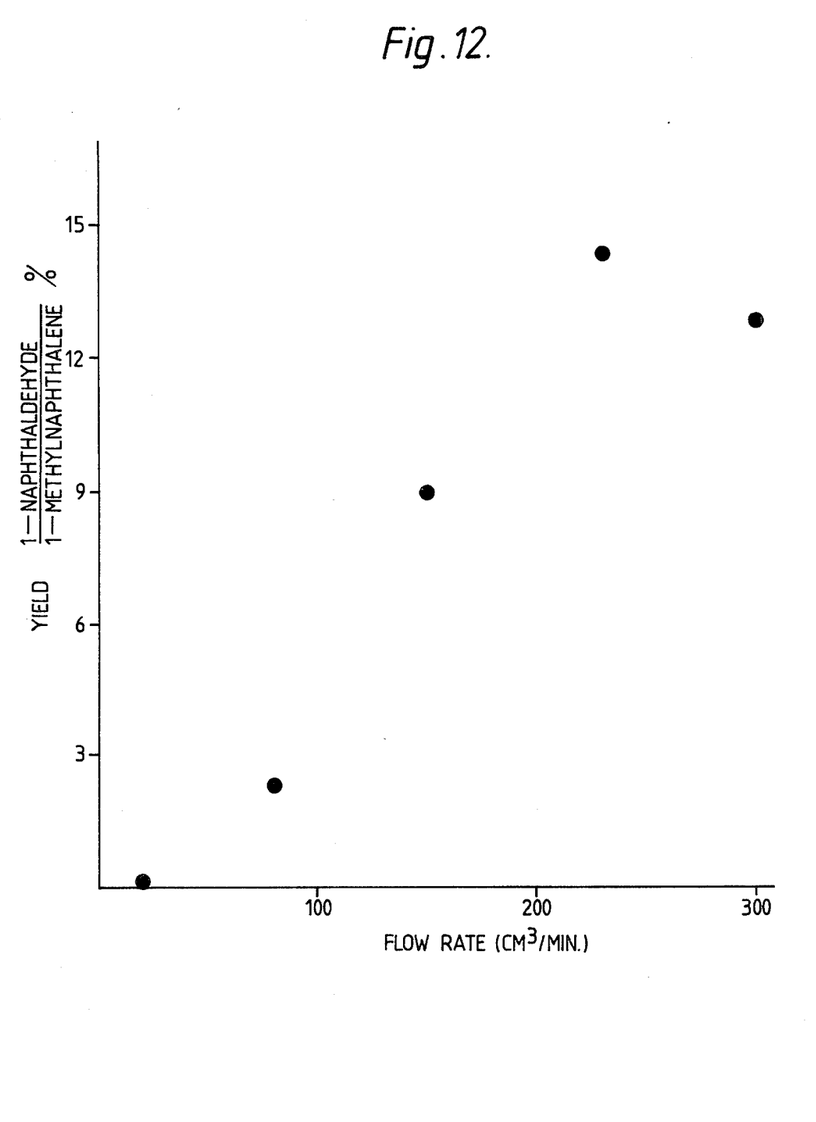

FIG. 12 shows how the yield of 1-naphthaldehyde varies (all other parameters being held constant) against the flow rate (shown in the abcissa in ml min$^{-1}$) of the aqueous liquid in the cell of FIG. 1. The first point represents a barely continuous, even an interrupted, flow; the middle three points a relatively streamline well-established jet; and the last point a very rapid flow tending to entrain the reactant 11 and perhaps for that reason lowering the yield.

REACTION 2

Oxidation of 1-methoxynaphthalene

Co(III) sulphate was generated as in Reaction 1. When this is allowed to react with 1-methoxynaphthalene, no side chain oxidation reaction occurs. Instead of dimer 4,4'-dimethoxybinaphthyl is produced as the only isolated product:

4 g (23 mmol) of the 1-methoxynaphthalene was allowed to react for 21 hours (current=200 mA) with electrochemically produced Co(III) sulphate at 20° C. (23° C. gave similar results.) The electrolyte solution was composed of 0.10M Co(II) sulphate in 2.5M H$_2$SO$_4$. The organic material isolated from the run was placed on a silica gel column, which was eluted with a solution of 5% ether in petroleum ether (bp=60°–80° C.). The initial band consisted of 3.42 g (19.6 mmol, 86%) of starting material. The second band gave a sticky solid that was washed with petroleum ether, yielding 80 mg 4,4'-dimethoxybinaphthyl.

REACTION 3

Oxidation of 1-naphthylmethanol 1-naphthylmethanol (500 mg, 3.2 mmol) in 2 g tributylphosphate was allowed to react with electrochemically produced Co(III) sulphate at 24° C. in the cell of FIG. 1 but having a U-tube format, i.e. lacking the crank 23. (This cell was also used in the following reactions, unless otherwise stated.) The electrolyte solution was composed of 0.12M Co(II) sulphate in 2M H$_2$SO$_4$. After 27 hours at 200 mA, no starting material remained as shown by thin-layer chromatography. The organic material isolated from this run was placed on a silica gel column, which was eluted with a 20% ether in petroleum ether (bp=60°–80° C.) solution. The initial band gave 326 mg (2.09 mmol, 66%) of 1-naphthaldehyde. A second band gave 14 mg (0.08 mmol, 2%) of a yellow solid which was identified as 1-naphthoic acid by its infrared spectrum and mass spectrum. After recrystallization from ether-petroleum ether, colourless needles were obtained that had a melting point of 158°–162° C. (authentic sample mp=158°–162° C.).

REACTION 4

Oxidation of 1-methyl-4-nitronaphthalene 500 mg (2.6 mmol) of 1-methyl-4-nitronaphthalene in 2.5 g tributylphosphate was allowed to react for 24 hours (current=200 mA) with electrochemically produced Co(III) sulphate at 37°–40° C. The electrolyte was composed of 0.10M Co(II) sulphate in 2.5M H$_2$SO$_4$. From the acidified base wash of the isolated reaction mixture, there was obtained 64 mg of a brown solid. This was boiled with charcoal in ether and then recrystallized from ether-petroleum ether. A few milligrams of a light yellow solid were obtained that had a melting point of 190°–210° C. The mass spectrum showed a peak corresponding to the molecular weight of 4-nitro-1-naphthoic acid (literature mp=219°–220° C.).

The material not extracted by the base wash was placed on a silica gel column which was eluted with a solution of 20% ether in petroleum ether (bp=60°–80° C.). The initial band gave 248 mg (1.3 mmol, 50%) of the 4-nitro-1-naphthaldehyde. After recrystallization from petroleum ether, the solid had a melting point of 110°–112° C. (literature mp=106°–107° C.).

REACTION 5

Oxidation of 1-ethylnaphthalene 2 g (12.8 mmol) of 1-ethylnaphthalene in 2 g of tributylphosphate was allowed to react for 21 hours (current=400 mA) with electrochemically produced Co(III) sulphate at 37°–40° C. The electrolyte solution was composed of 0.10M Co(II) sulphate in 2.5M H$_2$SO$_4$. The organic material isolated from the run was placed on a silica gel column, which was eluted with a solution of 10% ether in petroleum ether (bp=60°–80° C.). The initial band gave 1.35 g (8.6 mmol, 67%) of starting material. The second band gave 127 mg of a 3-component mixture, which was subjected to preparative thin-layer chromatography using a silica gel plate and a 5% ether-in-petroleum-ether solvent system. The plate was developed seven times and showed three major bands when exposed to ultraviolet light. The initial band gave 1 mg of an unknown material. The second band gave 63 mg (0.37 mmol, 9%) of 1-acetylnaphthalene as shown by a comparison of its infrared spectrum with that of an authentic sample. The third band gave 7 mg of a multi-component mixture.

REACTION 6

Oxidation of toluene

An excess of toluene was allowed to react with electrochemically produced Co(III) sulphate at 37°-40° C. As toluene is volatile and the cell was open-topped, fresh toluene had to be added occasionally. The electrolyte was composed of 0.1M Co(II) sulphate in 2.5M H₂SO₄. The reaction was run for 28½ hours at 400 mA, and in another run for 33 hours at 200 mA. The organic material isolated from the run was subjected to preparative thin-layer chromatography using silica plates and a 7.5% ether-in-petroleum-ether (bp=60°-80° C.) solvent system. One major band was obtained, which yielded 30 mg (0.3 mmol) of benzaldehyde (0.08 mmol in the other run) as shown by comparison of its infra-red spectrum with that of an authentic sample.

REACTION 7

Oxidation of m-phenoxytoluene 2 g (11 mmol) of m-phenoxytoluene in 2 g of tributylphosphate was allowed to react with electrochemically produced Co(III) sulphate at 37°-40° C. The electrolyte solution was composed of 0.1M Co(II) sulphate in 2.5M H₂SO₄. The reaction was run for 33 hours at 200 mA. The organic material isolated from the run was placed on a silica gel column, which was eluted with a solution of 5% ether in petroleum ether (bp=60°-80° C.). The initial band gave 1.5 g (8 mmol, 73%) of starting material. The elution solvent was changed to 10% ether in petroleum ether. A second band gave 15 mg (0.08 mmol, 2.6%) of a colourless liquid which was shown to be the aldehyde.

REACTION 8

Oxidation of p-cymene 5 g (37 mmol) of p-cymene was allowed to react with electrochemically produced Co(III) sulphate at 37°-40° C. The electrolyte solution was composed of 0.01M Co(II) sulphate in 2.5M H₂SO₄. The reaction was run for 21 hours at 200 mA. From the acidified base wash of the isolated reaction mixture, there was obtained 39 mg of a colourless solid. This was heated to 120° C. at 0.5 torr to remove any volatile materials. The remaining material was shown to be terephthalic acid (0.23 mmol) by a comparison of its melting point and infrared spectrum with those of an authentic sample. The organic material not extracted by the base wash was placed on a silica gel column, which was eluted with a solution of 5% ether in petroleum ether (bp=60°-80° C.). The initial band yielded p-cymene, while the second band gave a mixture of two components; this mixture was placed on a second silica gel column, which was eluted with a solution of 2.5% ether in petroleum ether, yielding an initial band consisting of 32 mg (0.2 mmol) of p-isopropylbenzaldehyde and a second band consisting of 62 mg (0.46 mmol) of a p-methylacetophenone. The reaction had thus been

REACTION 9

Oxidation of 9-methylanthracene 510 mg (2.6 mmol) of 9-methylanthracene in 2.5 mg of tributylphosphate was allowed to react with electrochemically produced Co(III) sulphate at 37°-40° C. The electrolyte solution was composed of 0.01M Co(II) sulphate in 2.5M H₂SO₄. The reaction was run for 22 hours at 200 mA. The organic material isolated from the run was placed on a silica gel column, which was eluted with a solution of 10% ether in petroleum ether (bp=60°-80° C.). The initial band gave 388 mg (2 mmol, 77%) of starting material. The second band gave 25 mg (0.13 mmol, 22%) of anthraquinone.

REACTION 10

1-methylnaphthalene with Ag(II) sulphate 2 g (14 mmol) of 1-methylnaphthalene in 2 ml of tributylphosphate was allowed to react with electrochemically produced Ag(II) sulphate at 23° C. The electrolyte solution was composed of 0.02M Ag(I) sulphate in 1.5M H₂SO₄. The reaction was run for 26 hours at 200 mA. The organic material isolated from the run was placed on a silica gel column, which was eluted with petroleum ether (bp=60°-80° C.) then with a solution of 1% ether in petroleum ether. From this column there were obtained 1.2 g (8.4 mmol, 60%) of starting material and 92 mg (0.32 mmol, 4.6%) of 4,4'-dimethylbinaphthyl.

REACTION 11

Nitration of 1-methylnaphthalene 2 g (14 mmol) of 1-methylnaphthalene in 2 ml of tributylphosphate was allowed to react with an electrolyzed solution of 5M HNO₃ at 20° C. The reaction was run for 22 hours at 200 mA. The organic material isolated from the run was placed on a silica gel column, which was eluted with a solution of 5% ether in petroleum ether (bp=60°-80° C.). The initial band yielded 1.21 g (8.5 mmol, 61%) of starting material. The second band yielded 500 mg of a yellow oil which consisted of 4 isomers of nitro-1-methylnaphthalene. This oil was subjected to preparative thin-layer chromatography on silica gel plates which were repeatedly developed with petroleum ether. The initial band yielded a brown solid, which was recrystallized from petroleum ether to give brown leafy crystals with a melting point of 63°-65° C. This material was identified as 8-nitro-1-methylnaphthalene (literature mp=65° C.). The second band gave an oil which consisted of a mixture of compounds. The third band yielded a yellow solid which was recrystallized from petroleum ether to give yellow needles with a melting point of 69.5°-71° C. This material was identified as 4-nitro-1-methylnaphthalene (literature mp=71° C.).

We claim:

1. A method of performing a chemical reaction between a reactive species and a reactant, comprising flowing a liquid including the precursor of the reactive species past an electrode for forming the reactive species from its precursor, causing the liquid to flow out of the influence of the electrode and out of the influence of anything else that would react with the reactive species, and within 100 milliseconds contacting the liquid with a volume of liquid comprising the reactant, the two liquids being substantially immiscible, whereby the reactive species reacts preferentially with the reactant.

2. A method according to claim 1, wherein the liquid is caused to flow out of the influence of the electrode as aforesaid immediately after passing the electrode.

3. A method according to claim 1, wherein the flow leaving the electrode and/or contacting the volume is streamline.

4. A method according to claim 1, wherein the flow leaving the electrode and/or contacting the volume is turbulent.

5. A method according to claim 1, wherein the counterelectrode is disposed upstream of the said electrode.

6. A method according to claim 5, wherein the counterelectrode is disposed such that no electrolysis of the reactant occurs.

7. A method according to claim 6, wherein the flow leaving the electrode is streamline and wherein the counterelectrode is so disposed in the flow, that the liquid which has contacted it makes no, or negligible, contact with the reactant.

8. A method according to claim 1, wherein the electrode is a conducting orifice.

9. A method according to claim 1, wherein the electrode comprises a plurality of orifices arranged in parallel and electrically interconnected.

10. A method according to claim 1, wherein the electrode is anodic.

11. A method according to claim 1, wherein the reactive species is in aqueous solution.

12. A method according to claim 11, wherein the reactive species is selected from the group consisting of lead ion, cerium ion, manganese ion, silver ion and cobalt ion.

13. A method according to claim 1, wherein the reactant is organic.

14. A method according to claim 13, wherein the reactant is selected from the group consisting of 1-alkylnaphthalene, 1-alkylnaphthalene, 1-alkoxynaphthalene, 1-naphthylalkanol, toluene, substituted toluene, cymene or methylanthracene.

15. A method according to claim 1, wherein the reactant is nonconductive.

16. A method according to claim 1, wherein the reactive species is continuously regenerated in a recirculating system.

17. A method according to claim 1, wherein the reactant is less dense than, and insoluble in, the said precursor, and floats as a layer on a volume of the precursor.

18. A method according to claim 1, wherein the liquid contacts the volume within 50 milliseconds of leaving the electrode.

19. A method according to claim 18, wherein the liquid contacts the volume substantially 30 milliseconds after leaving the electrode.

20. A method according to claim 18, wherein the liquid contacts the volume within 20 milliseconds, preferably within 10 milliseconds, of leaving the electrode.

* * * * *